United States Patent
Swisher et al.

(10) Patent No.: US 6,659,987 B2
(45) Date of Patent: Dec. 9, 2003

(54) FILL SPOUT FOR A DRAINAGE DEVICE

(75) Inventors: David R. Swisher, St. Charles, MO (US); Tony Lewis, St. Charles, MO (US); Eugene F. Schrader, St. Louis, MO (US); Michael D. Hudspeth, Arnold, MO (US)

(73) Assignee: Sherwood Services AG, Schaffhausen (CH)

( * ) Notice: Subject to any disclaimer, the term of this patent is extended or adjusted under 35 U.S.C. 154(b) by 94 days.

(21) Appl. No.: 09/981,088

(22) Filed: Oct. 16, 2001

(65) Prior Publication Data

US 2002/0072722 A1 Jun. 13, 2002

Related U.S. Application Data

(60) Provisional application No. 60/251,725, filed on Dec. 6, 2000.

(51) Int. Cl.[7] .................................................. A61M 1/00
(52) U.S. Cl. ........................................ 604/319; 604/321
(58) Field of Search ................................ 604/319–325, 604/541, 317, 318; 222/461; 141/331

(56) References Cited

U.S. PATENT DOCUMENTS

| | | | |
|---|---|---|---|
| 4,112,948 A | | 9/1978 | Kurtz et al. |
| 4,439,190 A | | 3/1984 | Protzmann et al. |
| 4,465,483 A | * | 8/1984 | Weilbacher .................. 604/317 |
| 4,544,370 A | | 10/1985 | Elliott et al. |
| 4,747,843 A | | 5/1988 | Felix et al. |
| 4,767,417 A | | 8/1988 | Boehringer et al. |
| 5,300,050 A | | 4/1994 | Everett, Jr. et al. |
| 5,988,447 A | * | 11/1999 | Yaski .......................... 222/158 |
| 2002/0173757 A1 | * | 11/2002 | Swisher et al. ............. 604/317 |

FOREIGN PATENT DOCUMENTS

| | | |
|---|---|---|
| DE | 908 229 | 7/1949 |
| EP | 0 402 117 A2 | 12/1990 |

* cited by examiner

*Primary Examiner*—Weilun Lo
*Assistant Examiner*—Michael Bogart
(74) *Attorney, Agent, or Firm*—Ari M. Bai; Greensfelder, Hemker & Gale, P.C.

(57) ABSTRACT

A fill spout for a drainage device is disclosed which permits the user to supply water directly to a water seal chamber of the drainage device for establishing a water seal therein. The fill spout comprises a funnel having lateral sides for facilitating the entry of the water into the drainage device, a depending lip extending from the fill spout for preventing any run off or spillage, and a tab having an arcuate-shaped rest which permits the user to open and close the fill spout. In use, the user pulls the tab which opens the fill spout and places a water-filled bottle against the rest. The user then pours a predetermined amount of water through the funnel and directly into the water seal chamber.

30 Claims, 5 Drawing Sheets

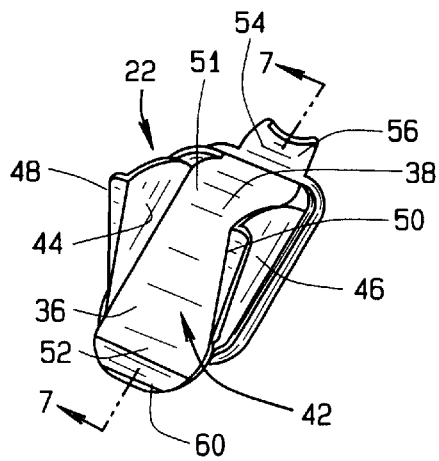
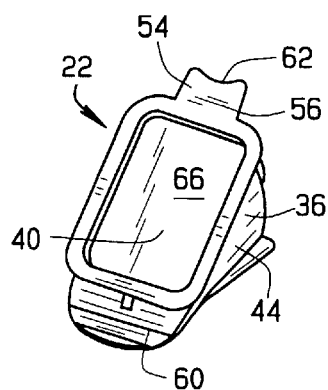
FIG. 4
FIG. 5
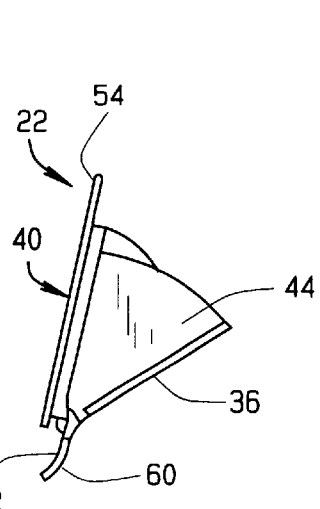
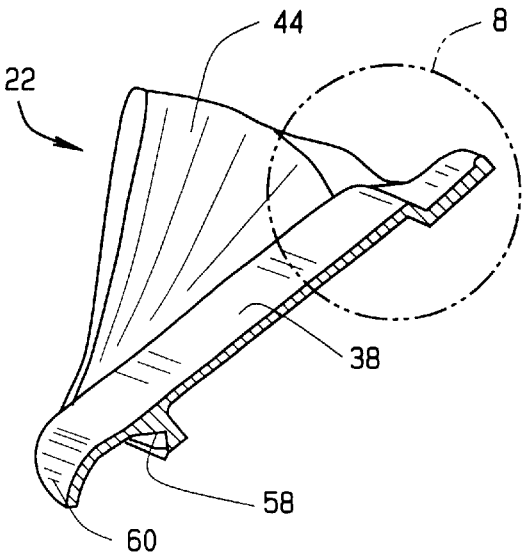
FIG. 6
FIG. 7
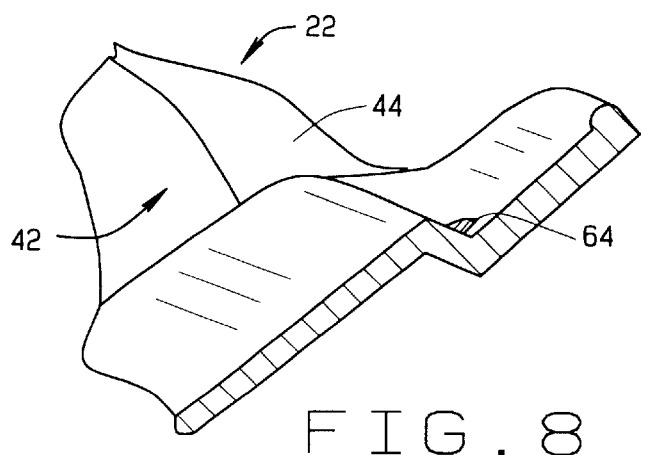
FIG. 8

FILL SPOUT FOR A DRAINAGE DEVICE

CROSS REFERENCE TO RELATED APPLICATIONS

This application claims benefit of U.S. Provisional Application No. 60/251,725, filed Dec. 6, 2000.

BACKGROUND OF THE INVENTION

1. Field of the Invention

The present invention relates to a chest drainage system, and particularly to a chest drainage device for suctioning gases and liquids from the chest cavity of a patient. More specifically, the present invention relates to an apparatus for directly accessing a water seal chamber of the chest drainage device.

2. Prior Art

A chest drainage device is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various respiratory infections can cause build up of liquid and gases around the lungs in the intrapleural space. When this happens, it causes the lungs to collapse to a volume much less than that of the pleural cavity, thereby severely impairing the breathing functions of the patient. The lungs can be re-expanded to their normal state to fill the pleural cavity by draining the liquid and gases from the pleural cavity using a chest drainage device.

There are many kinds of chest drainage devices used to drain the pleural cavity of a patient. One kind of drainage device, sometimes referred to as a "three-bottle" type, is illustrated in U.S. Pat. No. 3,363,626 to Bidwell et al. entitled "Underwater Drainage Apparatus". The "three-bottle" type drainage device has three interconnecting chambers which comprise: (1) a collection chamber for collecting liquids and gases suctioned from the patient's pleural cavity through a catheter; (2) an underwater seal chamber which communicates with the collection chamber and has a water seal which acts as a one way valve for passing gases collected from the patient's pleural cavity to the atmosphere; and (3) a suction control chamber for limiting the maximum suction (or negative pressure) applied to the patient's pleural cavity.

In operation, a source of vacuum is applied to the Bidwell et al. device such that the negative pressure generated in the collection chamber causes shed liquid and gases from the patient's pleural cavity to collect inside the collection chamber. As the liquid and gases enter the collection chamber, the vacuum establishes a fluid pathway which causes the collected gases to pass from the collection chamber and through the water seal of the water seal chamber. Once through the water seal, the gases are evacuated from the drainage device through a vacuum port which is in communication with the water seal chamber.

Another kind of drainage device is the "four-bottle system" which includes the three chambers of the "three-bottle system" and adds a fourth chamber, referred to as a safety seal/manometer chamber. Unlike the three bottle system of the prior art, the manometer chamber provides an accurate indicia of the level of suction being applied to the pleural cavity being drained.

Other drainage devices utilize a waterless means, such as a mechanical regulator, to adjust the level of vacuum applied to the collection chamber of the device. Such "dry" drainage devices which employ a mechanical regulator may also include either a liquid-filled manometer or a dry manometer that does not require any liquid to operate. However, either type of "dry" drainage device must have either a water seal or a one way valve in order to prevent the reflux of evacuated gases back into the collection chamber.

Prior to operating drainage devices having a water seal, the user must first supply a predetermined amount of water inside the water seal chamber for establishing a water seal therein. For example, the AQUA-SEAL chest drainage device manufactured by Tyco Healthcare Group, LP of Mansfield, Massachusetts uses a funnel attached to an elastic hollow tubing having one end attached to the funnel and the other end connected to a vacuum port of the drainage device. In operation, the user occludes the tubing by kinking it and then fills the funnel with a water seal. Once the funnel is filled to a predetermined level, the user unkinks the tubing and allows the water seal to flow into the water seal chamber through the vacuum port of the drainage device. Although the above apparatus and method for supplying the water seal to the water seal chamber has proven adequate, it requires that vacuum being applied to the drainage device be interrupted which can cause an undesirable build up of liquids and gases in the patient's intrapleural space. Further, the practitioner must supply a funnel and tube arrangement or other similar external device to provide the water seal to the water seal chamber.

Therefore, there is a need in the art for a drainage device which provides an apparatus and method for easily and effectively supplying a water seal to the water seal chamber without interrupting vacuum being applied to the device. There is a further need in the art for a drainage device having a fill spout which provides direct access to the water seal chamber when supplying the water seal without having to use an external device to accomplish the same.

OBJECTS AND SUMMARY OF THE INVENTION

The primary object of the present invention is to provide a drainage device having a fill spout for supplying a water seal to a water seal chamber.

Another object of the present invention is to provide a fill spout which directly communicates with the water seal chamber.

A further object of the present invention is to provide a fill spout that is configured to rest substantially flush against the body of the drainage device when the fill spout is placed in the closed position.

Yet another object of the present invention is to provide a fill spout that does not require an external arrangement in order to supply a liquid water seal to the water seal chamber.

Another further object of the present invention is to provide a fill spout that prevents the water seal from running along the underside of the fill spout when the water seal is being supplied to the water seal chamber.

Yet another further object of the present invention is to provide a fill spout that is configured to facilitate the direct entry of a water seal into the water seal chamber of a drainage device without interrupting vacuum being applied to the device.

Another further object of the present invention is to provide a fill spout that does not require an external device to access the water seal chamber.

In brief summary, the present invention overcomes and substantially alleviates the deficiencies present in the art by providing a fill spout for a drainage device which allows a water seal to be supplied directly to the water seal chamber.

Preferably, the drainage device comprises a unitary casing having a collection chamber for the collection of liquids and gases, a water seal chamber in communication with the collection chamber for preventing evacuated gases from reentering the collection chamber, and a mechanical regulator for regulating the degree of vacuum inside the drainage device. The collection chamber is in fluid flow communication with a patient's pleural cavity through a catheter having one end disposed inside the patient and the other end attached to a collection port of the collection chamber. The water seal chamber defines a compartment having one end in communication with the collection chamber and the other end in communication with a source of vacuum. A water seal, preferably water, is disposed along the bottom of the water seal chamber. The water seal acts as a one-way barrier that prevents the reflux of evacuated gases back into the collection chamber during a sudden high negative pressure condition in the collection chamber, for example, when a patient takes a quick and deep inhalation. According to one aspect of the present invention, the water seal is supplied by using a fill spout which communicates directly with the water seal chamber and facilitates the entry of the water seal therein.

The fill spout of the present invention is adapted to rotatably engage an aperture formed in the casing of the drainage device and comprises a body having opposing top and bottom sides defining a distal end and a proximal end. The top side includes a funnel for facilitating the pouring of a liquid water seal into the water seal chamber, while the bottom side forms a rectangular-shaped recess which is exposed when the fill spout is placed in the closed position. The funnel comprises an opening at the proximal end of the body for inserting a water-filled container therethrough and a depending lip formed at the distal end for preventing the water seal from running along the bottom side of the funnel when pouring the water seal through the funnel. Moreover, the funnel further comprises opposing lateral sides which extend outwardly from the body of the fill spout with each lateral side having a stop formed along the edge thereof. The stop is adapted to abut the interior of the casing and prevents any further movement of the fill spout when it is placed in the open position by the user. The body further includes an integral tab having a rest that extends in the proximal direction and provides a means for grasping a portion of the body by a user when opening and closing the fill spout. To facilitate the pouring of the water seal into the funnel, the distal end of the tab forms an arcuate-shaped rest which is adapted to prop the container while the water seal is being poured into the water seal chamber. A groove type sealing surface for establishing a fluid tight seal with the recessed area of the fill spout formed around the aperture is provided about the entire periphery of the fill spout body. Finally, a hinge pin in the form of a slot is defined between the distal end of the body and the depending lip for pivoting the fill spout between open and closed positions relative to the aperture.

In assembly, the fill spout is mounted inside the aperture adjacent the water seal chamber such that the hinge pin rotatably engages the lower lip of the aperture and pivots the fill spout between open and closed positions. In the closed position, the bottom side of the fill spout is substantially flush with the casing and fluid flow communication is prevented through the aperture. When the user places the fill spout in the open position he or she simply grasps and pulls the tab outwardly which exposes the aperture. The user then places the container on the rest of the tab and pours a predetermined amount of water seal through the funnel and into the water seal chamber. Once the procedure is completed, the user closes the fill spout and the drainage device may be operated.

These and other objects of the present invention are realized in the preferred embodiment, described by way of example and not by way of limitation, which provides for a drainage device having a fill spout which permits the user to supply a water seal directly to the water seal chamber.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 4 is a perspective view of the fill spout showing the top side thereof according to the present invention;

FIG. 5 is a perspective view of the fill spout showing the bottom side thereof according to the present invention;

FIG. 6 is a side view of the fill spout according to the present invention;

FIG. 7 is a cross sectional view of the fill spout taken along line 7—7 of FIG. 4 according to the present invention;

FIG. 8 is an enlarged view of FIG. 7 showing the groove seal of the fill spout according to the present invention.

DETAILED DESCRIPTION OF THE INVENTION

Figure 2:
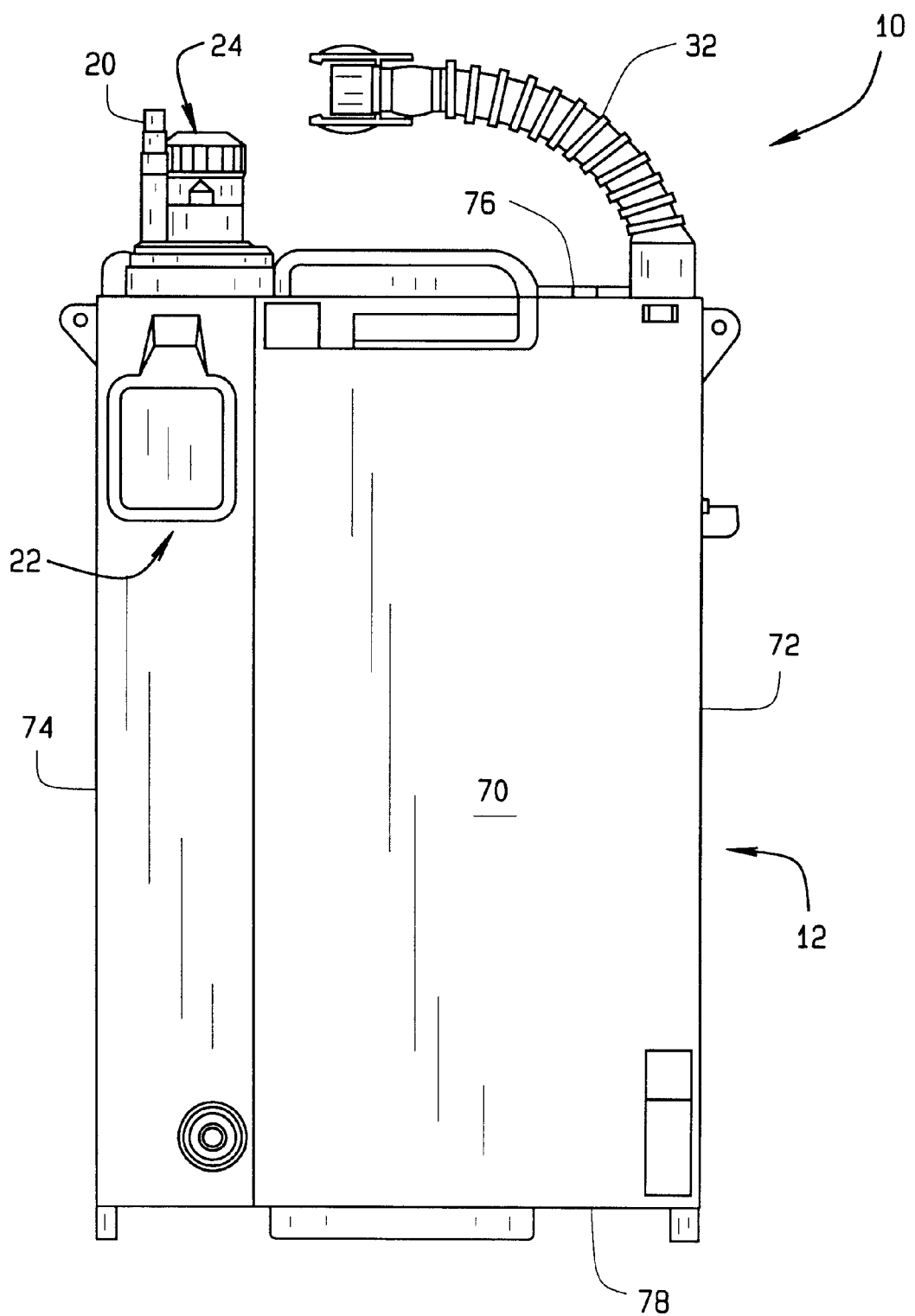
FIG. 2 is a rear view of the drainage device showing the fill spout in the closed position according to the present invention.

Referring to the drawings, the preferred embodiment of the fill spout used with the drainage device 10 of the present invention is illustrated and generally indicated as 22 in FIG. 2. Drainage device 10 comprises a casing 12 defined by a front wall 68, rear wall 70 (FIG. 2), top wall 76, bottom wall 78, and opposing side walls 72 and 74. As shown, casing 12 is further defined by a collection chamber 14 for the collection of shed fluids from a patient's pleural cavity, a water seal chamber 16 in communication with the collection chamber 14 for preventing reflux of evacuated gases back to the patient, and a suction control chamber (not shown) in communication with the water seal chamber 16 for regulating the degree of vacuum inside drainage device 10.

Preferably, drainage device 10 further comprises a vacuum port 20 attached to a vacuum regulator 24 which is in fluid flow communication with a vacuum source (not shown). The vacuum regulator 24 allows the user to adjust the level of negative pressure applied to device 10, while a negative pressure relief valve 28 is provided along top wall 76 for venting any excess negative pressure from inside casing 12. As further shown, a collection port 26 in communication with the collection chamber 14 is attached to patient tubing 32 which transports shed blood and gases from the patient's pleural cavity and into the collection chamber 14.

When vacuum is applied by the vacuum regulator 24 to drainage device 10, liquid 34 and gases (not shown) are drawn from the patient's pleural cavity and deposited into collection chamber 14 through collection port 26. Once the liquid 34 and gases are deposited inside drainage device 10, the vacuum applied to vacuum port 20 draws the gases from the collection chamber 14 and through the water seal 30 of the water seal chamber 16. As the evacuated gases pass through the water seal chamber 16, the vacuum source forces the gases out the vacuum port 20 for proper disposal.

Figure 1:
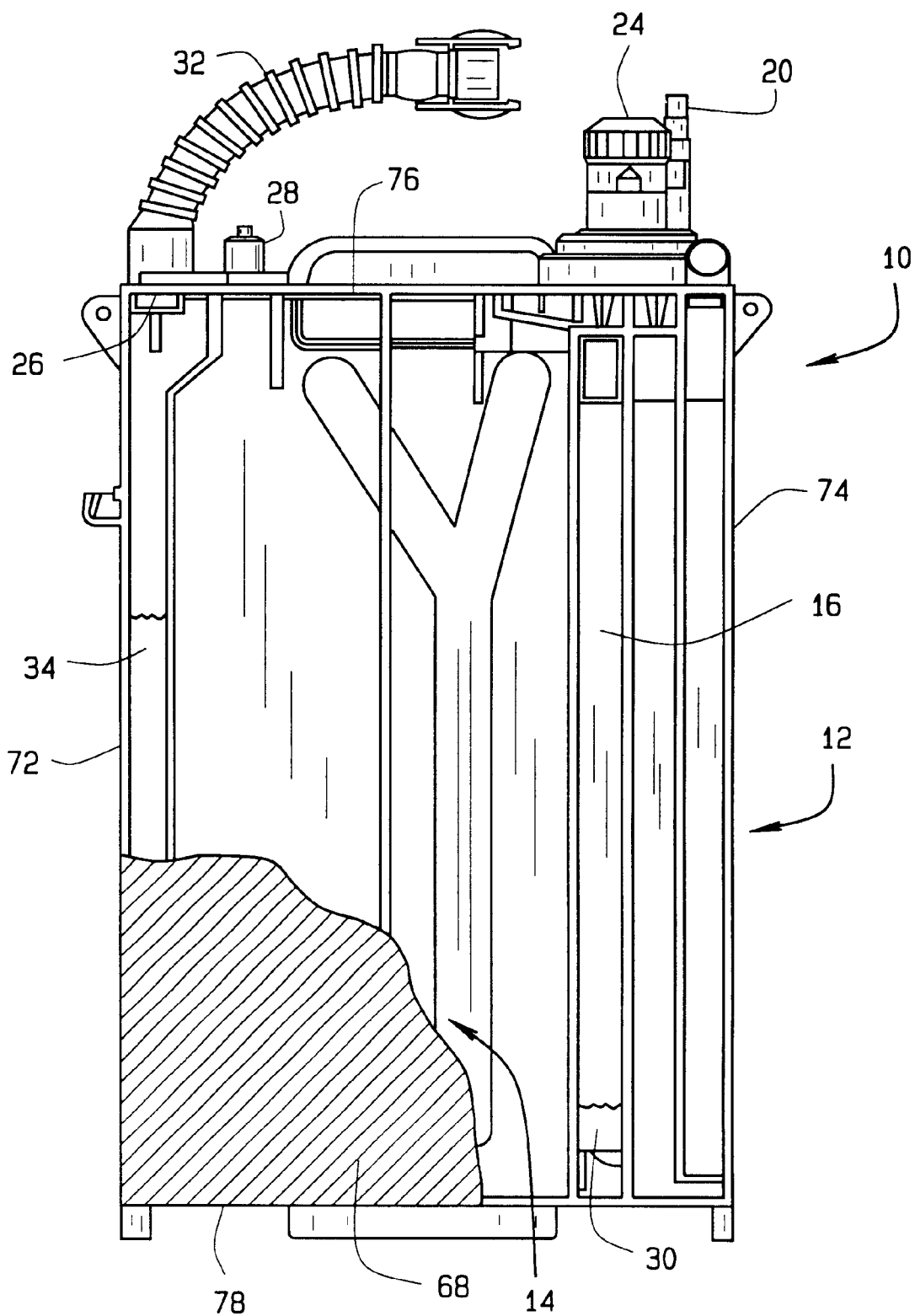
FIG. 1 is a front view of the drainage device according to the present invention.
Figure 3:
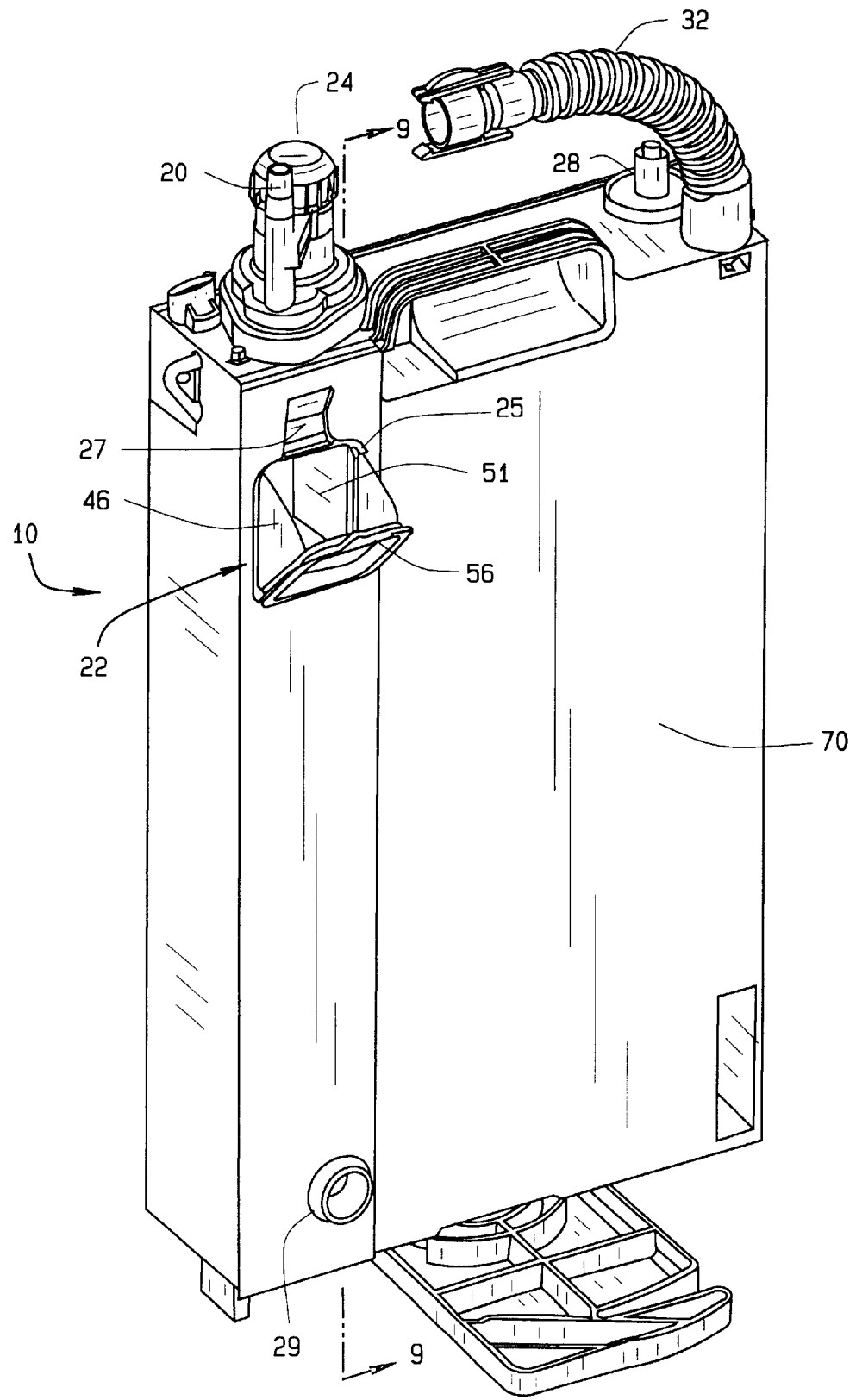
FIG. 3 is a perspective view of the fill spout shown in the open position according to the present invention.

Referring to FIG. 2, fill spout 22 of the present invention provides a means for supplying a water seal 30 (FIG. 1) directly to the water seal chamber 16. Fill spout 22 is sized and shaped to securely engage against an aperture 25 (FIG. 3) formed through the rear wall 70 of drainage device 10 and may be placed in either an open position (FIG. 3) or a closed position (FIG. 2) by a user. Referring to FIG. 3, a recessed area 27 is formed around the periphery of aperture 25 for seating a pull tab 56 of fill spout 22 therein when fill spout 22 is placed in the closed position.

As illustrated in FIGS. 4–8, fill spout 22 comprises a body 36 having opposing top and bottom sides 38, 40 defining a distal end 52 and a proximal end 54, respectively. Top side 38 includes a funnel 42 for facilitating the pouring of a water seal 80 (FIG. 9) into the water seal chamber 16, while bottom side 40 forms a rectangular-shaped recess 66. Referring specifically to FIG. 4, funnel 42 comprises opposing lateral sides 44 and 46 which extend outwardly from body 36 with stops 48 and 50 formed along the edge of each lateral side 44 and 46, respectively. Stops 48 and 50 are adapted to abut the interior portion of rear wall 70 and prevent any further movement of body 36 when fill spout 22 is being placed in the open position by the user. As further shown, lateral sides 44 and 46 define an opening 51 at the proximal end 54 of body 36 for entry of water seal 80 through aperture 25.

Referring to FIG. 5, distal end 52 of body 36 defines a depending lip 60 which is sized and shaped to prevent water seal 80 from running along the bottom side 40 of fill spout 22 when poured through funnel 42. One of skill in the art can appreciate that the configuration of lip 60 will direct any water seal 80 entering funnel 42 directly into the water seal chamber 16, thereby preventing any running or spillage of water seal 80 along bottom side 40. As shown in FIG. 8, the periphery of funnel 42 forms a groove seal 64 formed around the entire periphery of body 36 and provides a fluid tight seal against recess area 27 when fill spout 22 is placed in the closed position.

Referring back to FIG. 5, the proximal end 54 of body 36 defines pull tab 56 which may be grasped between a user's thumb and forefinger in order to place the fill spout 22 in an open position. The pull tab 56 further defines an arcuate-shaped rest 62 which provides the user with a means of propping a container 82 containing water seal 80 on rest 62 in order to facilitate direct entry of water seal 80 through the opening 51 of funnel 42 and into water seal chamber 16. It should be appreciated by one of ordinary skill in the art that other types of containers, such as a bottle, cup or the like, may be used to supply water seal 80 without departing from the spirit and scope of the present invention. As further shown, pull tab 56 is sized and shaped to be received into the recessed area 27 such that it rests generally flush with rear wall 70 and permits sufficient space for a user to grasp the top portion of pull tab 56 when opening or closing fill spout 22.

Figure 9:
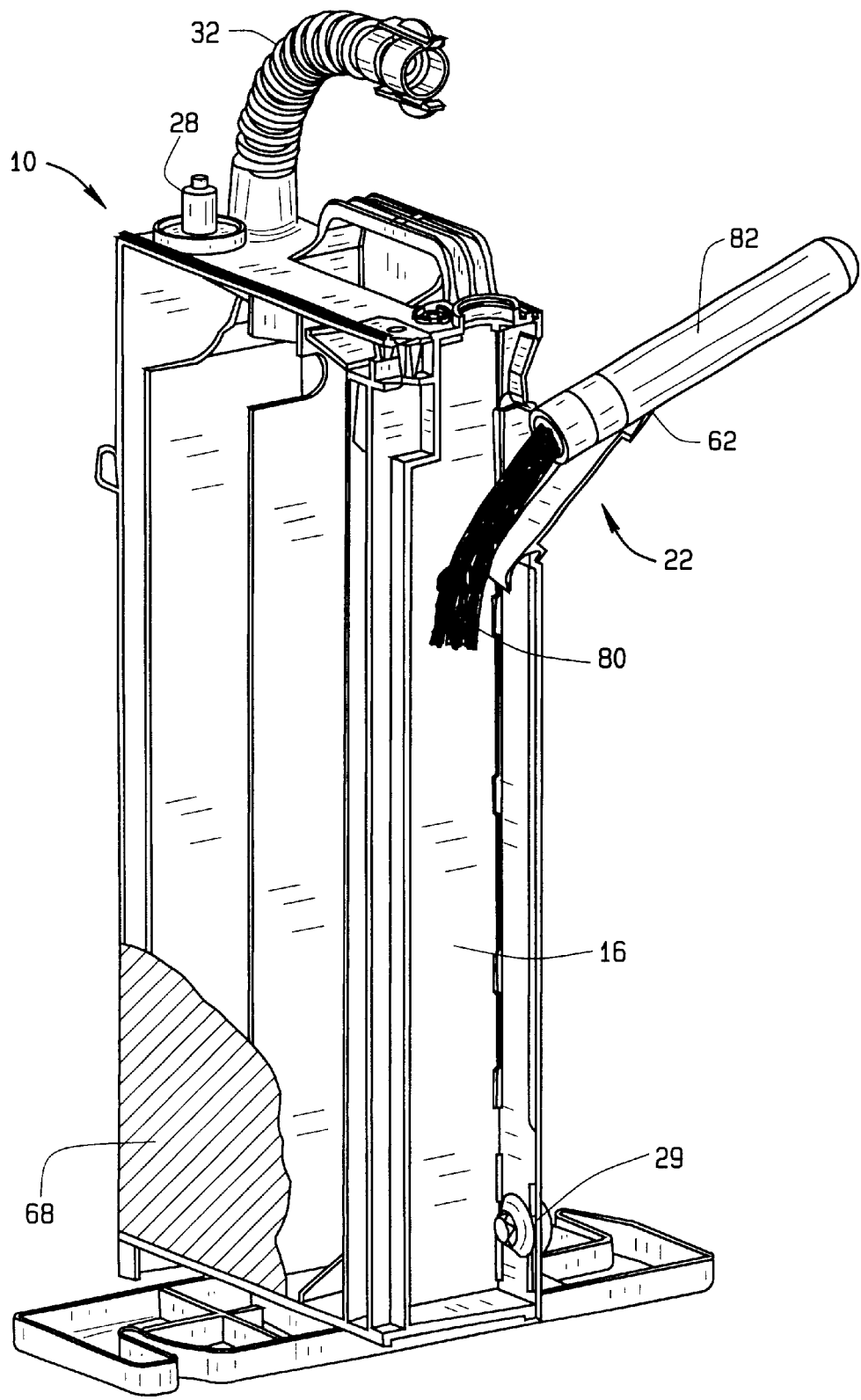
FIG. 9 is a cross-sectional view of the drainage device taken along line 9—9 of FIG. 3 illustrating the method of using the fill spout according to the present invention.

As illustrated in FIGS. 6 and 7, the space between depending lip 60 and bottom side 40 defines a hinge 58 in the form of a slot which is adapted to rotatably engage aperture 25 when closing and opening fill spout 22. When the user opens fill spout 22 by pulling tab 56, stops 48 and 50 eventually abut against the interior of rear wall 70 which prevents any further movement of filling spout 22 and exposes funnel 42 to the user. Referring to FIG. 9, the user then places the container 82 against rest 62 and pours a predetermined amount of the water seal 80 down funnel 42 and into the water seal chamber 16. Once the water seal 30 has been established, the user returns the fill spout 22 to the closed position.

Although fill spout 22 is preferably used with drainage device 10 having a mechanical regulator as described above, the present invention contemplates that other drainage devices, such as those devices having a water-filled suction control chamber or a water manometer in combination with a mechanical regulator, are also felt to fall within the spirit and scope of the present invention.

Another aspect of the present invention is the provision for a water seal access port 29 (FIG. 3) having a mechanical one way valve (not shown) of conventional design adapted to engage a needle-less syringe (not shown). In operation, the user engages the water seal access port 29 with the needle-less syringe in order to remove any excess water seal 80 or alternatively add more water seal 80 to the water seal chamber 16.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. A drainage device comprising:
   a casing having a collection chamber for the collection of fluids, a water seal chamber in communication with said collection chamber for preventing reflux of fluids back into said collection chamber, and a suction control chamber for regulating the degree of vacuum inside said casing;
   an aperture formed through said casing adjacent said water seal chamber, said aperture being in direct communication with said water seal chamber; and
   a fill spout disposed along said aperture, said fill spout being operable between a closed position wherein said aperture is closed to fluid flow and an open position where said aperture is open to fluid flow, wherein said fill spout comprises a body having an opposing top and bottom sides defining a distal end and a proximal end, said top side including a funnel, said funnel facilitating the pouring of a liquid through said aperture.

2. The drainage device according to claim 1, wherein said funnel includes opposing lateral sides which extend outwardly from said body.

3. The drainage device according to claim 2, wherein each of said lateral sides has a stop adapted to abut against said casing when said fill spout is placed in the open position.

4. The drainage device according to claim 2, wherein said funnel further includes opposing lateral sides which define an opening at said proximal end of said body.

5. The drainage device according to claim 1, wherein said body further includes a lip at said distal end adapted to prevent any liquid from running along said bottom side of said body when said liquid is poured through said funnel.

6. The drainage device according to claim 1, wherein said body defines a tab for placing said fill spout between said open and closed positions.

7. The drainage device according to claim 6, wherein said tab forms a rest for propping a container thereon.

8. The drainage device according to claim 7, wherein said rest has a generally arcuate shape.

9. The drainage device according to claim 1, wherein said bottom side defines a recess.

10. The drainage device according to claim 1, wherein said body further includes a hinge adapted to rotatably engage said aperture and place said fill spout between said open and closed positions.

11. The drainage device according to claim 1, wherein said aperture includes a periphery defining a recessed area and said funnel defines a groove seal around the periphery thereof, said groove seal being adapted to engage said recessed area in a fluid tight seal when said fill spout is placed in the closed position.

12. In combination a fill spout and a drainage device comprising:
- a casing having a plurality of interconnected chambers, at least one of said plurality of interconnected chambers being a water seal chamber adapted to receive a liquid water seal therein,
- an aperture formed through said casing in direct communication with said water seal chamber; and
- a fill spout engageable with said aperture, said fill spout including a body having top and bottom sides defining distal and proximal ends, said top side defining a funnel adapted to direct fluid flow through said aperture, said funnel having opposing lateral sides which extend outwardly from said body, said fill spout being operable between a closed position wherein said aperture is closed to fluid flow and an open position wherein said aperture is open to fluid flow.

13. A fill spout engageable to an aperture in a casing of a drainage device having a water seal chamber, comprising:
- a body, said body having opposing top and bottom sides defining a distal and a proximal end, said top side including a funnel, said funnel having opposing lateral sides which extend outwardly from said body, said body being operable between a closed position, and an open position, wherein said open position of said water seal chamber is accessible through said funnel.

14. The fill spout according to claim 13, wherein each of said lateral sides includes a respective stop formed along the edge thereof.

15. The fill spout according to claim 14, wherein said stops are adapted to abut said vessel and prevent further movement of said body.

16. The fill spout according to claim 13, wherein said bottom side forms a recess.

17. The fill spout according to claim 13, wherein said body includes a tab.

18. The fill spout according to claim 17, wherein said tab defines an arcuate-shaped rest.

19. The fill spout according to claim 13, wherein said distal end defines a lip.

20. The fill spout according to claim 19, wherein said body further includes a hinge defined between said distal end and said lip.

21. A medical drainage device comprising:
- a casing, said casing including first, second and third intercommunicating chambers, said second chamber including a water seal to define during normal operation a first pressure differential, said third chamber in communication with a source of vacuum for applying a second pressure differential with said first and second chambers for establishing a unidirectional flow from said first and second chambers to atmosphere,
- a fill spout in selective communication with said second chamber, said fill spout being operable to provide fluid flow communication with said second chamber, wherein said casing defines an aperture, said fill spout being engageable with said aperture, said fill spout having a body, said body defines a funnel for providing fluid flow communication with said second chamber.

22. The medical drainage device according to claim 21, wherein said funnel comprises opposing lateral sides.

23. The medical drainage device according to claim 22, wherein said funnel further comprises a lip located transverse to said opposing lateral sides.

24. The medical drainage device according to claim 21, wherein said body further defines a tab, said tab being adapted to place said fill spout between open and closed positions.

25. The medical drainage device according to claim 24, wherein said tab extends outwardly from said body.

26. The medical drainage device according to claim 24, wherein said tab defines a rest, said rest having a means for propping a container for providing a water seal to said second chamber.

27. The medical drainage device according to claim 21, wherein said body defines a seal, said seal being operable to maintain a fluid tight engagement with said aperture.

28. The medical drainage device according to claim 21, wherein said fill spout is positionable between an open position wherein said second chamber is accessible by a user and a closed position where said second chamber is not accessible by a user.

29. The medical drainage device according to claim 21, wherein said fill spout is rotatable within said aperture between said open and closed positions.

30. A method for providing a water seal to a water seal chamber of a medical drainage device, said medical drainage device having a casing comprising a collection chamber for the collection of fluid in communication with the water seal chamber for establishing unidirectional flow from said collection chamber to atmosphere, the water seal chamber being in communication with a suction control chamber for regulating the degree of vacuum applied to said collection chamber, said casing defining an aperture in direct communication with said water seal chamber, a fill spout being engageable to said aperture, the fill spout being operable between an open position and a closed position, said fill spout including a tab, the method comprising the steps of:
 a) grasping the tab of the fill spout;
 b) placing the fill spout in the open position;
 c) placing a fluid container on said fill spout;
 d) pouring fluid from said fluid container, through said fill spout and into said water seal chamber; and
 e) placing the fill spout in the closed position.

* * * * *